United States Patent [19]
Kaiser et al.

[11] 3,939,164
[45] Feb. 17, 1976

[54] 7 AND 8-HALO SUBSTITUTED 1,2,3,4-TETRAHYDROISOQUINOLINE COMPOUNDS

[75] Inventors: Carl Kaiser, Haddon Heights, N.J.; Robert G. Pendleton, Elkins Park, Pa.

[73] Assignee: SmithKline Corporation, Philadelphia, Pa.

[22] Filed: Feb. 8, 1974

[21] Appl. No.: 440,925

[52] U.S. Cl............ 260/286 R; 260/283 R; 424/258
[51] Int. Cl.².............. C07D 217/08; C07D 217/00
[58] Field of Search......... 260/286 R, 283 R, 287 R

[56] References Cited
UNITED STATES PATENTS

| | | | |
|---|---|---|---|
| 2,785,166 | 3/1957 | Cusic............................. | 260/286 R |
| 2,876,223 | 3/1959 | Bloom............................. | 260/256.4 |
| 2,998,422 | 8/1961 | Cavallito et al................. | 260/286 R |
| 3,134,673 | 5/1964 | Ganguin et al.................. | 260/286 R |
| 3,314,963 | 4/1967 | Kock................................. | 260/288 |
| R28,034 | 6/1974 | Gray................................. | 260/283 S |

OTHER PUBLICATIONS

R. Benson and Schiele, "Tranquilizing and Antidepressive Drugs," 1962, pp. 13, 14.

*Primary Examiner*—Donald G. Daus
*Assistant Examiner*—David E. Wheeler
*Attorney, Agent, or Firm*—Joan S. Keps; Richard D. Foggio; William H. Edgerton

[57] ABSTRACT

1,2,3,4-Tetrahydroisoquinoline compounds having 7 and 8 halo substituents are inhibitors of phenylethanolamine N-methyltransferase.

4 Claims, No Drawings

7 AND 8-HALO SUBSTITUTED 1,2,3,4-TETRAHYDROISOQUINOLINE COMPOUNDS

This invention relates to new 1,2,3,4-tetrahydroisoquinoline compounds having 7 and 8 halo substituents. These compounds have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

Also, the compounds of this invention produce a reduction in food consumption and are therefore useful in the treatment of obesity.

The compounds of this invention are represented by the following formula:

Formula I

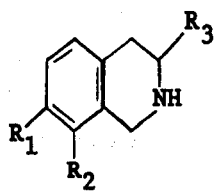

in which:

$R_1$ and $R_2$ are chloro, bromo, fluoro or iodo, $R_1$ and $R_2$ being the same or different and $R_3$ is hydrogen, methyl or ethyl and pharmaceutically acceptable, acid addition salts thereof.

Preferred compounds of this invention are represented by Formula I in which $R_1$ and $R_2$ are chloro. Advantageous compounds are represented by Formula I in which $R_1$ and $R_2$ are chloro and $R_3$ is hydrogen or methyl.

A particularly preferred compound of this invention is 7,8-dichloro-1,2,3,4-tetrahydroisoquinoline hydrochloride.

The compounds of this invention are prepared by the following procedure:

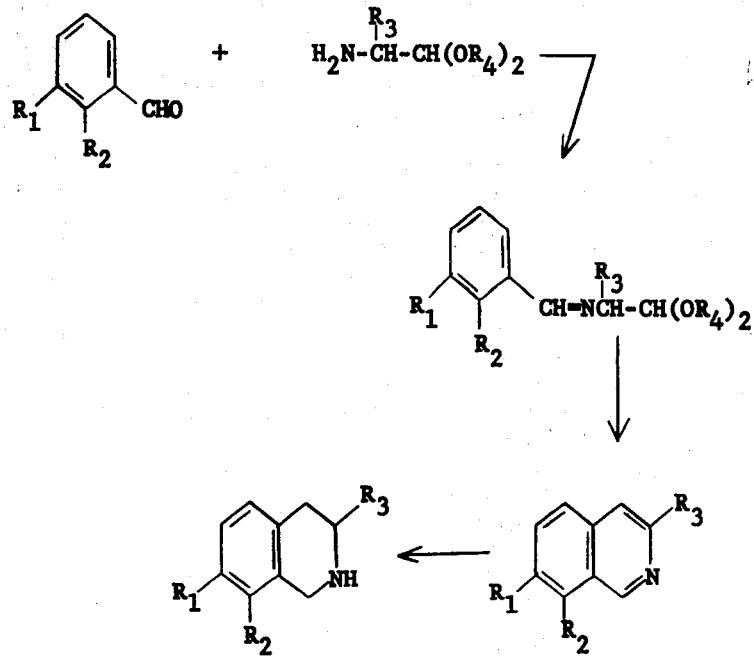

The terms $R_1$, $R_2$ and $R_3$ are as defined above and $R_4$ is methyl or ethyl.

According to the above procedure, the 7,8-substituted isoquinolines are prepared by the Pomeranz-Fritsch reaction, that is by the reaction of a 2,3-substituted benzaldehyde with a 2,2-di-lower alkoxyethylamine and acid catalyzed cyclization of the resulting 2,2-di-lower-alkoxy-N-(2,3-substituted-benzylidene)ethylamine. The benzaldehyde and the 2,2-di-lower-alkoxyethylamine are preferably reacted in an organic solvent such as toluene at elevated temperature, for example at reflux temperature. The cyclization is carried out with an acid catalyst such as sulfuric acid and phosphorus pentoxide.

The 7,8-substituted isoquinolines are hydrogenated using a hydrogenation catalyst such as platinum oxide to give the 7,8-substituted-1,2,3,4-tetrahydroisoquinolines of this invention.

The pharmaceutically acceptable, acid addition salts of the compounds of Formula I are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The activity of the compounds of this invention is demonstrated by inhibition of phenylethanolamine N-methyltransferase in vitro, by the assay procedure described by Pendleton and Snow, *Molecular Pharmacology* 9:718–725 (1973), at concentrations of about $1.2 \times 10^{-7}$M. For example, at a concentration of $1.2 \times 10^{-7}$M, a preferred compound of this invention 7,8-dichloro-1,2,3,4-tetrahydroisoquinoline inhibits phenylethanolamine N-methyltransferase by 50%.

In addition, the activity of the compounds of this invention is demonstrated by administration to rats and squirrel monkeys at doses of about 10-100 mg./kg. orally to produce reduction of levels of epinephrine in the adrenal glands.

The compounds of this invention are administered internally either parenterally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The following examples are not limiting but are illustrative of the compounds of this invention and processes for their preparation.

EXAMPLE 1

A mixture of 65.7 g. (0.375 m.) of 2,3-dichlorobenzaldehyde and 39.4 g. (0.375 m.) of 2,2-dimethoxyethylamine was refluxed azeotropically in 150 cc. of toluene. When all the water was removed (1-2 hours), the solution was concentrated and distilled to give 2,2-dimethoxy-N-(2,3-dichlorobenzylidene)ethylamine, b.p. 140°C. (0.7 mm.).

Ten grams (0.0382 m.) of 2,2-dimethoxy-N-(2,3-dichlorobenzylidene)ethylamine was added dropwise to 100 cc. of concentrated sulfuric acid with stirring at 0°–5°C. The solution was added to a mixture of 5 g. of phosphorus pentoxide and 5 cc. of concentrated sulfuric acid. The mixture was stirred and heated at 160°C. for 20 minutes, then cooled to 140°C., maintained there for 20 minutes, then cooled to 100°C. and quenched on ice. The mixture was filtered and the filtrate, with cooling, was made basic with 40% aqueous sodium hydroxide solution, then cooled and extracted with ether. The ether was removed from the extract to give 7,8-dichloroisoquinoline as the residue. The 7,8-dichloroisoquinoline was dissolved in acetone. Ethereal hydrogen chloride in slight excess was added to give, after filtering, 7,8-dichloroisoquinoline hydrochloride which after recrystallizing from ethanol melted at 225°–6°C.

The above prepared 7,8-dichloroisoquinoline hydrochloride was reduced in two portions, using 0.7 g. of platinum oxide in 100 cc. of methanol, for 1 hour at ambient temperature. The mixture was filtered and concentrated. The residue was converted to the base using ammonium hydroxide and was extracted into ether. The extract was dried with magnesium sulfate, filtered and concentrated to give, as the residue, 7,8-dichloro-1,2,3,4-tetrahydroisoquinoline.

The above prepared base was dissolved in about 50 cc. of ethanol. Ethereal hydrogen chloride in slight excess was added, then excess ether was added and the solid filtered to give 7,8-dichloro-1,2,3,4-tetrahydroisoquinoline hydrochloride, m.p. 221°–222°C.

EXAMPLE 2

Bromine (168 g., 1.05 m.) is added over about one hour, with vigorous stirring, to 117.5 g. (0.47 m.) of 2,3-dibromotoluene at 190°C. After the addition is complete, the mixture is cooled to 100°C., then 120 cc. of concentrated sulfuric acid is added and the mixture is stirred for one hour at 100°C. Temperature is raised to 140°C. for 5 minutes, then the mixture is cooled and the reaction is quenched in ice water. The solid is extracted into ether, and the ether extract is washed with water, then dilute aqueous sodium bicarbonate until the acid is completely removed, and filtered. Removing the ether by evaporation gives 2,3-dibromobenzaldehyde as the residue.

Using 2,3-dibromobenzaldehyde in place of 2,3-dichlorobenzaldehyde in the procedure of Example 1 gives 7,8-dibromo-1,2,3,4-tetrahydroisoquinoline.

EXAMPLE 3

In the procedure of Example 1, using 2,3-difluorobenzaldehyde in place of 2,3-dichlorobenzaldehyde gives, as the product, 7,8-difluoro-1,2,3,4-tetrahydroisoquinoline.

EXAMPLE 4

By the procedure of Example 2, the following halo substituted toluene compounds:
  2-bromo-3-chlorotoluene
  3-bromo-2-chlorotoluene
  2-chloro-3-iodotoluene
  3-chloro-2-iodotoluene
are converted to the corresponding halo substituted benzaldehydes and these benzaldehydes are used as starting materials in the procedure of Example 1 to give the following products, respectively:
  8-bromo-7-chloro-1,2,3,4-tetrahydroisoquinoline
  7-bromo-8-chloro-1,2,3,4-tetrahydroisoquinoline
  8-chloro-7-iodo-1,2,3,4-tetrahydroisoquinoline
  7-chloro-8-iodo-1,2,3,4-tetrahydroisoquinoline.

EXAMPLE 5

2,3-Diiodobenzoic acid is treated with diborane in tetrahydrofuran to give 2,3-diiodobenzyl alcohol which is oxidized to 2,3-diiodobenzaldehyde with activated manganese dioxide in methylene chloride.

Using 2,3-diiodobenzaldehyde in place of 2,3-dichlorobenzaldehyde as the starting material in the procedure of Example 1 gives 7,8-diiodo-1,2,3,4-tetrahydroisoquinoline.

EXAMPLE 6

Using 2-bromo-3-iodobenzoic acid as the starting material in the procedure of Example 5 gives 8-bromo-7-iodo-1,2,3,4-tetrahydroisoquinoline.

By the same procedure, using 3-bromo-2-iodobenzoic acid as the starting material, 7-bromo-8-iodo-1,2,3,4-tetrahydroisoquinoline is prepared.

EXAMPLE 7

Using 2,2-diethoxy-1-methylethylamine in place of 2,2-dimethoxyethylamine in the procedure of Example 1, the product is 7,8-dichloro-3-methyl-1,2,3,4-tetrahydroisoquinoline.

Also, using 1-ethyl-2,2-dimethoxyethylamine, the product is 7,8-dichloro-3-ethyl-1,2,3,4-tetrahydroisoquinoline.

EXAMPLE 8

One gram of 7,8-dichloro-1,2,3,4-tetrahydroisoquinoline is dissolved in ethanol. A molar equivalent amount of maleic acid in ethanol is added. Ether is added and the precipitate is filtered off to give the maleate salt of 7,8-dichloro-1,2,3,4-tetrahydroisoquinoline.

By the same procedure, using citric acid, the citrate salt is prepared.

Reacting one gram of 7,8-dichloro-1,2,3,4-tetrahydroisoquinoline in ethanol with a molar equivalent amount of stearic acid, then adding water and filtering gives the stearate salt.

EXAMPLE 9

| Ingredients | Amounts |
|---|---|
| 7,8-Dichloro-1,2,3,4-tetrahydroisoquinoline hydrochloride | 150 mg. |
| Lactose | 350 mg. |

The ingredients are mixed and filled into a hard gelatin capsule.

What is claimed is:

1. A compound of the formula:

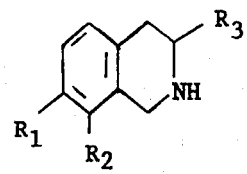

in which:
$R_1$ and $R_2$ are chloro, bromo or iodo, $R_1$ and $R_2$ being the same or different, or $R_1$ and $R_2$ are both fluoro and $R_3$ is hydrogen, methyl or ethyl or a pharmaceutically acceptable, acid addition salt thereof.

2. A compound of claim 1 in which $R_1$ and $R_2$ are chloro.

3. A compound of claim 1 in which $R_1$ and $R_2$ are chloro and $R_3$ is hydrogen or methyl.

4. The compound of claim 1, said compound being 7,8-dichloro-1,2,3,4-tetrahydroisoquinoline hydrochloride.

* * * * *